United States Patent [19]

Zanecchia et al.

[11] Patent Number: 5,534,952
[45] Date of Patent: Jul. 9, 1996

[54] PUPILLOMETER

[75] Inventors: Denise Zanecchia; Ann M. Heinrich, both of Fort Worth; Teresa Ustanik, Burleson, all of Tex.

[73] Assignee: Alcon Laboratories, Inc., Fort Worth, Tex.

[21] Appl. No.: 362,381

[22] Filed: Dec. 22, 1994

[51] Int. Cl.⁶ .............................. A61B 3/00; B42D 15/00
[52] U.S. Cl. .......................... 351/200; 33/555.1; 283/115
[58] Field of Search ..................................... 351/200, 205; 40/110, 112; 206/379; 434/187, 262, 271; 33/563, 565, 555.1, 555.2, 567, 512, 1 B; 283/48.1, 115, 900

[56] References Cited

U.S. PATENT DOCUMENTS

| | | | |
|---|---|---|---|
| 4,220,402 | 9/1980 | Jannelli | 351/231 |
| 4,406,285 | 9/1983 | Villasenor et al. | 33/1 B |
| 4,517,747 | 5/1985 | Morin | 33/512 X |
| 4,936,016 | 6/1990 | Simpson | 33/555.2 |
| 5,279,041 | 1/1994 | Wright | 33/379 |

OTHER PUBLICATIONS

Allergan Pharmaceuticals; "Optistick®"; 1975.
Rosenbaum Pocket Vision Screener; Merck Sharp & Dohme; 1992.
Rosenbaum Pocket Vision Screener; Alcon; 1993.

Primary Examiner—William L. Sikes
Assistant Examiner—Huy Mai
Attorney, Agent, or Firm—Jeffrey S. Schira

[57] ABSTRACT

A pupillometer made from a clear, flexible material and having at least one pair of semicircular reference marks.

8 Claims, 1 Drawing Sheet

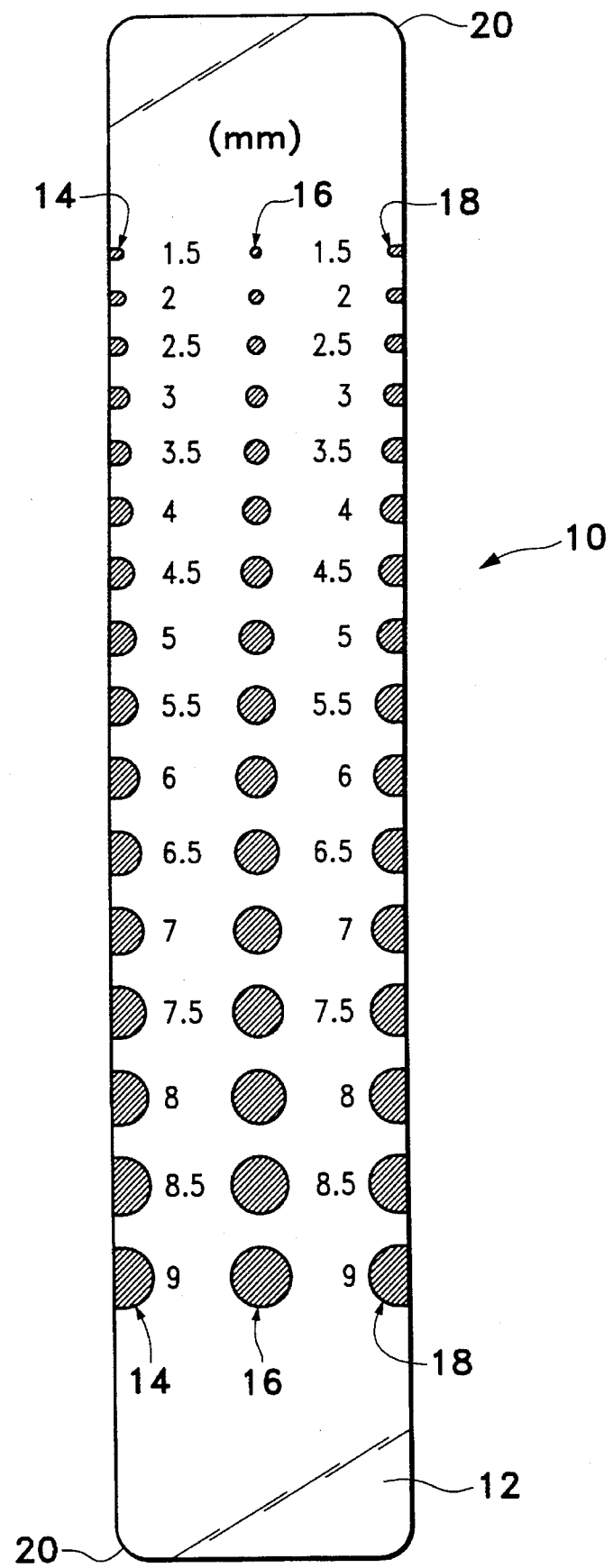

PUPILLOMETER

BACKGROUND OF THE INVENTION

The present invention relates to a device for measuring pupil diameter.

In a variety of ophthalmic diagnostic procedures, it is desirable to measure the diameter of the patient's pupil. The size of the human pupil is governed by the antagonistic actions of the dilator and sphincter muscles in the iris that are controlled by sympathetic and parasympathetic nerves, respectively. Several factors are known to affect pupil size, including retinal illuminance, the accommodative state of the lens and a variety of sensory and emotional conditions. The size of the pupil also tends to change with age, with elderly patients having relatively smaller pupils as a group. Size may also be influenced by certain diseases and conditions of ill health or pharmacological effects.

One problem associated with measuring pupil size is that the pupil is never entirely at rest but undergoes small, continuous oscillations known as hippus. As a result, to measure the pupil accurately requires measuring the pupil over a short period of time to determine an average pupil diameter. The measurement process is made more difficult by the natural body movements of the patient and the examiner. Other problems in achieving consistent pupil measurements in the same environment are control of illumination in the examining room. Light meters are often used to identify the amount of light available so as to assure similarity of conditions at different patient visits.

Prior art pupil measuring devices have included simple rulers graduated in millimeters and rulers having millimeter graduations on one side and circular or semicircular marks of fixed diameter on the other side. One such ruler is commonly referred to as the "Rosenbaum" ruler because it was designed by J. G. Rosenbaum, M.D. While these rulers were the most commonly used pupil measuring devices prior to the present invention, they had several disadvantages. For example, these rulers generally are printed on opaque cardstock, making it difficult to line up the graduations with the patient's eye. Patients also are more likely to move or become uncomfortable when a solid object is placed over the eye, creating a potential safety issue because of the hard, non-flexible material and sharp edges used in prior art pupillometers. In addition, prior art pupillometers contain only one set of either graduations or marks, requiring that the pupillometer be moved to measure alternate eyes. Such movement increases examination time and patient discomfort and that can be used quickly.

Accordingly, a need continues to exist for an accurate pupillometer that minimizes patient discomfort.

BRIEF DESCRIPTION OF THE INVENTION

The present invention improves upon prior art pupillometers by providing a pupillometer having a plurality of measuring marks imprinted on a clear substrate.

Accordingly, one objective of the present invention is to provide an accurate pupillometer.

Another objective of the present invention is to provide a pupillometer that increases patient comfort and safety.

These and other objectives and advantages of the present invention will become apparent from the detailed description and claims which follow.

BRIEF DESCRIPTION OF THE DRAWINGS

FIG. 1 is a plan view of the pupillometer of the present invention.

DETAILED DESCRIPTION OF THE INVENTION

Pupillometer 10 of the present invention generally consists of substrate 12 imprinted with a series of reference marks 14, 16 and 18. Substrate 12 may be approximately 4.5 centimeters wide and 23.5 centimeters long with a thickness of approximate 0.20 gauge. Preferably, substrate 12 has rounded corners 20. Substrate 12 may be made of any clear, flexible material such as rigid vinyl plastic.

Reference marks 14, 16 and 18 are preferably black, imprinted on substrate 12 using a silk screen process and sized in one half millimeter increments from about 1.5 mm to 9.0 mm, although different colors, printing processes and increments may also be used. During graphic printing processes, reference marks 14 and 18 should be printed slightly larger than the final outline of substrate 12 to ensure that marks 14 and 18 extend all the way to the edge of substrate 12.

In use, pupillometer 10 may be held between the patient's eyes so that marks 14 align vertically with the patient's right eye and marks 18 align vertically with the patient's left eye. The clear nature of substrate 12 allows the physician or technician to more easily align marks 14 and 18 and also serves to minimize patient discomfort.

This description is given for purposes of illustration and explanation. It will be apparent to those skilled in the relevant art that changes and modifications may be made to the invention described above without departing from its scope or spirit.

We claim:

1. A pupillometer, comprising:

a) a clear substrate; and b) at least two sets of semicircular reference marks on opposite edges of the substrate arranged so as to align with a patient's left and right eye, respectively.

2. The pupillometer of claim 1 wherein the substrate comprises rigid vinyl plastic.

3. The pupillometer of claim 1 further comprising a third set of circular reference marks intermediate the sets of semicircular reference marks.

4. The pupillometer of claim 1 wherein the substrate reference marks are sized between approximately 1.5 millimeters and 9.0 millimeters in one half millimeter increments.

5. The pupillometer of claim 1 wherein the reference marks are imprinted on the substrate using a silk screen process.

6. The pupillometer of claim 1 wherein the substrate is approximately 4.5 centimeters wide.

7. A pupillometer, comprising:

a) a clear substrate; and b) at least two sets of semicircular reference marks on opposite edges of the substrate arranged so as to align with a patient's left and right eye, respectively and sized between approximately 1.5 millimeters and 9.0 millimeters in one half millimeter increments and imprinted on the substrate using a silk screen process.

8. The pupillometer of claim 7 wherein the substrate is approximately 4.5 centimeters wide.

* * * * *